US00PP19241P3

(12) United States Plant Patent
van Kleinwee

(10) Patent No.: US PP19,241 P3
(45) Date of Patent: Sep. 16, 2008

(54) ***HELIOTROPIUM* PLANT NAMED 'HELIOSIL'**

(50) Latin Name: *Heliotropium arborescens*
Varietal Denomination: Heliosil

(75) Inventor: Theodorus Cornelis Maria van Kleinwee, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/651,393

(22) Filed: Jan. 9, 2007

(65) Prior Publication Data

US 2008/0184446 P1 Jul. 31, 2008

(51) Int. Cl.
*A01H 5/00* (2006.01)

(52) U.S. Cl. ..... Plt./438

(58) Field of Classification Search ..... Plt./438, Plt./226

See application file for complete search history.

*Primary Examiner*—Kent L. Bell
*Assistant Examiner*—June Hwu
(74) *Attorney, Agent, or Firm*—S. Matthew Edwards

(57) ABSTRACT

A distinct *Heliotropium* plant particularly distinguished by its light lavender color, vigor, good branching, and floriferous characteristics. The new cultivar can be used in 10–12 cm pots without use of growth regulators.

1 Drawing Sheet

Latin name of the genus and species of the plant claimed: *Heliotropium arborescens.*
Varietal denomination: 'Heliosil'.

BACKGROUND OF THE NEW PLANT

The present invention relates to a new distinct cultivar of *Heliotropium,* botanically known as *Heliotropium arborescens.*

The new cultivar resulted from open-pollination of a proprietary *Heliotropium arborescens* seedling identified as 'A260-1' not patented. 'A260-1' has longer flower stems, a less branching character, and smaller flowers than the new cultivar. Seeds of 'A260-1' were harvested in 2001 and the new variety 'Heliosil' was selected in 2002 as one of the plants of this population. Breeder's code of the new plant is 'D3235-1.'

This new plant is an annual. The new cultivar is a product of a planned breeding program conducted in Enkhuizen, The Netherlands. The new cultivar 'Heliosil' is a compact variety that flowers throughout the Summer. 'Heliosil' was asexually reproduced by cuttings for 4 years now and trialled under different conditions in Europe. It has retained its distinctive characteristics through successive propagations and is firmly fixed. The new variety reproduces true to type in successive generations of asexual reproduction.

DESCRIPTION OF THE DRAWING

This new *Heliotropium* plant is illustrated by the accompanying photographic drawing which shows blooms, buds and foliage of the plant in full color, the color shown being as true as can be reasonably obtained by conventional photographic procedures.

SUMMARY OF THE INVENTION

The new *Heliotropium* has not been observed under all possible environmental conditions. The phenotype may vary somewhat with variations in environment such as temperature and light intensity without, however, any variance in genotype.

The following characteristics have been repeatedly observed and are determined to be basic. characteristics of 'Heliosil' and distinguish the new *Heliotropium* as a new and distinct variety:

1. Good branching
2. Light lavender color
3. Vigorous plant habit
4. Freely flowering
5. Compact plant habit, even without the use of growth regulators

DESCRIPTION OF THE NEW CULTIVAR

The following detailed descriptions set forth the distinctive characteristics of this new *Heliotropium* plant. The data which define these characteristics were collected from asexual reproductions carried out in Enkhuizen, The Netherlands. The plant history was taken on 30 week old plants, grown in the open field in Enkhuizen, The Netherlands with day temperatures ranging from 16 and 30° Celsius, and night temperatures ranging from 10 to 16° Celsius.

Color references are primarily to the R.H.S. Colour Chart of The Royal Horticultural Society of London.

TABLE 1

DIFFERENCES BETWEEN THE NEW CULTIVAR 'HELIOSIL' AND TWO SIMILAR VARIETIES

| | 'Atlanta' (U.S. Plant Patent No. 11,326) | Marine GWO (Not patented) | 'Heliosil' |
|---|---|---|---|
| Plant height | 25 cm | 60 cm | 35-45 cm |
| Plant width | 40-45 cm | 45 cm | 60 cm |
| Branching | Freely branching | Poor branching | Freely branching |
| Foliage color | RHS 145A | RHS 138A | RHS 145A, old leaves RHS 146A |

TABLE 1-continued

DIFFERENCES BETWEEN THE NEW CULTIVAR 'HELIOSIL' AND TWO SIMILAR VARIETIES

| | 'Atlanta' (U.S. Plant Patent No. 11,326) | Marine GWO (Not patented) | 'Heliosil' |
|---|---|---|---|
| Inflorescence width | 9-13 cm | 22 cm | 10-14 cm |
| Flower color | Dark blue | Dark blue | Light lavender |
| Flower width | 8 mm | 7 mm | 8.5 mm |

The plant:

*Classification.*—Botanical: *Heliotropium arborescens.*

Parentage:

*Female parent.*—Proprietary seedling of *Heliotropium arborescens* 'A260-1,' not patented.

*Male parent.*—Unknown variety or seedling of *Heliotropium arborescens.*

Propagation:

*Type cuttings.*—Terminal cuttings.

*Root description.*—Fibrous.

*Rooting habit.*—Freely branching.

*Time to initiate roots.*—9–12 days at air temperature of 21° C.

*Time to develop roots.*—14–18 days at air temperature of 17° C.

Plant description:

*Growth habit.*—Upright.

*Plant.*—Height: 35–45 cm. Width: 60 cm.

*Behavior of plant outside under hot and cold conditions.*—Good.

*Branching character.*—Freely branching without pinching.

*Number of branches per plant.*—1–3 branches at base of plant+approximately 13 lateral branches.

*Crop time from rooting to finished plant.*—8 weeks.

The stem:

*Diameter.*—4.5 mm, up to 15 mm.

*Shape.*—Cylindrical.

*Length of.*—Plant stem: 34–45 cm when fully developed. Lateral branch: 35–45 cm when fully developed. Internode: 11 mm under high light conditions and 22 mm under low light conditions.

*Pubescence.*—Densely, short hairs.

*Color.*—Young stem: RHS 147B. Older stem: With anthocyanin pigmentation; RHS N199B matches best although the actual color is slightly lighter.

The foliage:

*Arrangement.*—Alternate.

*Number of leaves.*—2–25.

*Shape of leaf.*—Elliptic.

*Fragrance.*—Light scent of hay.

*Leaf.*—Apex: Acute. Base: Attenuate. Margin: Entire.

*Texture.*—Densely covered on lower and upper side with soft, short hairs.

*Leaf.*—Length: 6–11 cm. Width: 2–4 cm.

*Color.*—Upper side: Young leaf RHS 145A, old leaf RHS 146A. Lower side: Young leaf RHS 147C, old leaf RHS 148B.

*Petiole.*—Length: 12 mm. Color: In young and old leaf: RHS N144D. Diameter: 2 mm. Texture: Densely pubescent with short, soft hairs.

*Venation.*—Shape: Pinnate. Color: Upper and lower surface: RHS N144D.

Inflorescence:

*Flowering season.*—Continuous and free flowering throughout spring, summer and fall.

*Type.*—Terminal compound cymes.

*Height.*—3–4 cm.

*Width.*—2.5 cm when first flowers open 10–14 cm when flowering is finished.

*Number of open flowers per inflorescence.*—50–75.

*Peduncle.*—Strength: Strong. Aspect: At an angle of 45° to the stem. Length: 1–4 cm. Diameter: 1.5 cm. Texture: Densely pubescent. Color: RHS 197A.

*Fragrance.*—Strong.

*Lastingness of inflorescence on plant.*—4 weeks.

Flower:

*Shape.*—Funnel shaped.

*Length.*—6 mm.

*Width (of corolla).*—8.5 mm.

*Number of petals.*—5, fused at base, forming tube.

*Apex.*—Rounded.

*Margin.*—Entire.

*Texture.*—Upper side: Smooth. Lower side: Smooth, occasionally very short hairs, more hairs on veins.

*Color.*—Upper side: young flower: RHS N87D, old flower: RHS 85D, base RHS 150D. Lower side: young flower: RHS 85D, old flower: RHS 85D.

*Corolla tube.*—Length: 4 mm. Diameter at base: 1 mm. Diameter at tube opening: 1 mm. Texture outer surface: Some pubescence. Texture inner surface: Smooth. Color of outer surface: RHS 86A. Color of inner surface: RHS N199A.

*Sepals.*—Number: 5, fused at base. Shape: Deltoid. Length: 3 mm. Width: Average 0.5 mm. Apex: Acute to acuminate. Margin: Entire. Texture: Upper and lower surface densely pubescent with long soft hairs. Color: RHS 147A.

*Bud.*—Shape: Tubular. Length: 4 mm. Diameter: 1 mm. Color: RHS 85C.

Androecium:

*Anther.*—Color: RHS N199D. Length: 1.5 mm. Shape: Ligulate.

*Stamen.*—Number: 5, fused to inside of tube. Length: 0.3 mm.

*Pollen color.*—RHS 155A.

*Amount of pollen.*—Abundant.

Gynoecium:

*Pistil.*—Number: One. Length: 2.5 mm.

*Style.*—Length: 0.4 mm. Color: RHS 154C.

*Ovary.*—Number: One per pistil. Size: 0.4 mm diameter, 1.1 mm long. Color: RHS 143C.

*Stigma.*—Shape: Capitate. Color: RHS 143C, top RHS 154B.

Seed:

*Production.*—Yes.

*Size.*—Length: 1–1.5 mm. Diameter: 1 mm.

*Color.*—RHS 200A.

*Shape.*—Ovoid.

Disease resistance and tolerance for weather conditions: Good tolerance to heat. No specific susceptibility for pests or diseases has been observed to date.

What is claimed is:

1. A new and distinct variety of *Heliotropium* plant, substantially as illustrated and described herein.

* * * * *

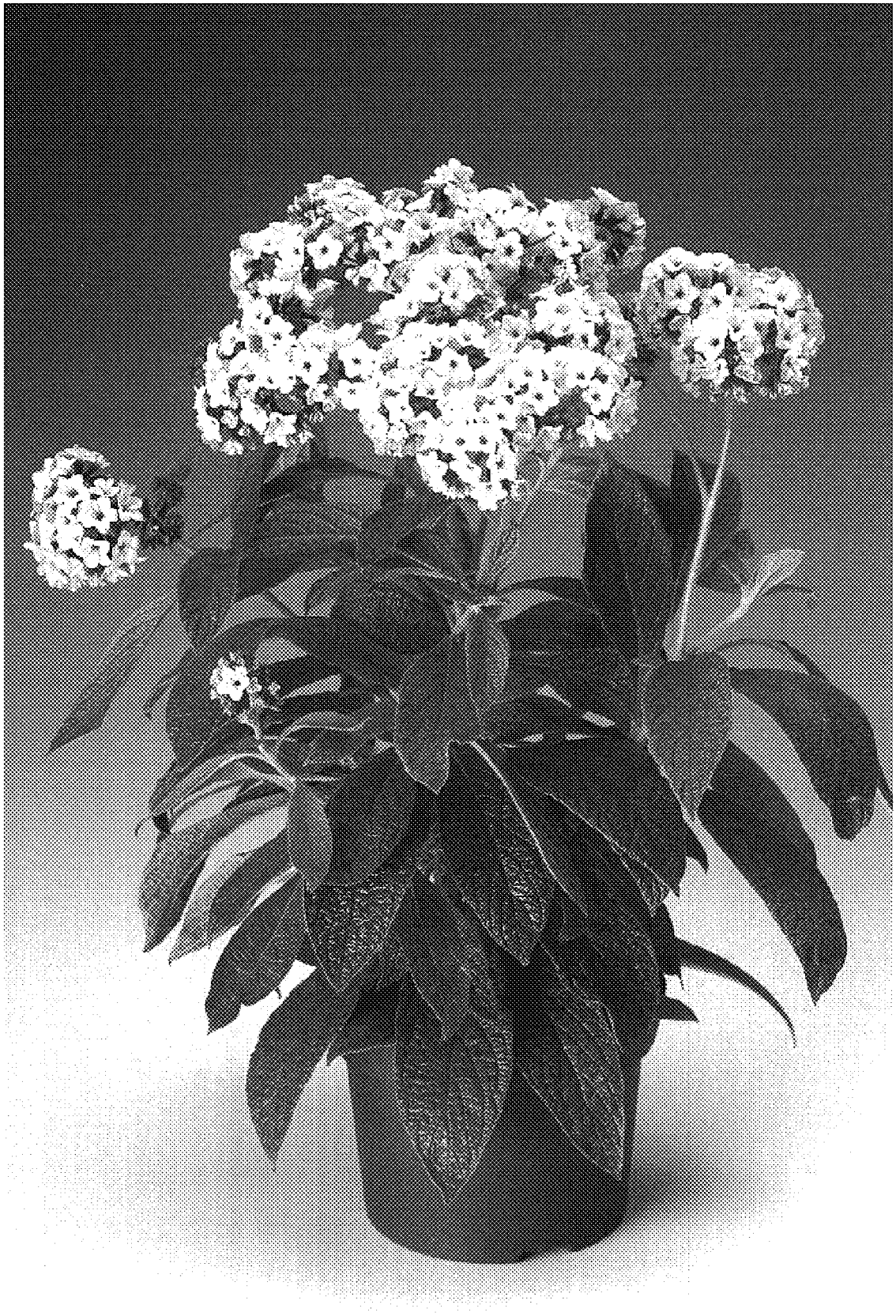

UNITED STATES PATENT AND TRADEMARK OFFICE

CERTIFICATE OF CORRECTION

PATENT NO. : PP 19,241 P3
APPLICATION NO. : 11/651393
DATED : September 16, 2008
INVENTOR(S) : Theodorus Cornelis Maria van Kleinwee It is certified that error appears in the above-identified patent and that said Letters Patent is hereby corrected as shown below:

At column 1, line 12, delete "'A260-1'" and insert therefor --'A260-1,'--

At column 2, line 4, delete "basic." and insert therefor --basic--

At column 3, under "The stem:" and after "Length of-Plant stem:", delete "34-45" and insert therefor --35-45--

Signed and Sealed this

Eleventh Day of November, 2008

JON W. DUDAS
*Director of the United States Patent and Trademark Office*